US00PP27027P3

(12) United States Plant Patent
Musacchi et al.

(10) Patent No.: US PP27,027 P3
(45) Date of Patent: Aug. 9, 2016

(54) PEAR TREE NAMED 'PE4UNIBO'

(50) Latin Name: ***Pyrus communis* L.**
Varietal Denomination: PE4UNIBO

(71) Applicant: Alma Mater Studiorum—Università di Bologna, Bologna (IT)

(72) Inventors: Stefano Musacchi, Wenatchee, WA (US); Vincenzo Ancarani, Bologna (IT); Silviero Sansavini, Bologna (IT)

(73) Assignee: Alma Mater Studiorum—Università di Bologna, Bologna (IT)

( * ) Notice: Subject to any disclaimer, the term of this patent is extended or adjusted under 35 U.S.C. 154(b) by 94 days.

(21) Appl. No.: 14/121,608

(22) Filed: Sep. 24, 2014

(65) Prior Publication Data

US 2015/0327418 P1 Nov. 12, 2015

(30) Foreign Application Priority Data

May 9, 2014 (QZ) ..... PBR 2014/0972

(51) Int. Cl.
*A01H 5/08* (2006.01)

(52) U.S. Cl.
USPC ..... Plt./176

(58) Field of Classification Search
USPC ..... Plt./176
See application file for complete search history.

(56) References Cited

PUBLICATIONS

PLUTO Plant Variety Database Feb. 19, 2016. p. 1.*

* cited by examiner

*Primary Examiner* — Annette Para
(74) *Attorney, Agent, or Firm* — Foley & Lardner LLP

(57) ABSTRACT

A new and distinct *Pyrus communis* L. pear tree variety named 'PE4UNIBO' is particularly characterized by the following features: medium vigorous trees with semi-upright habit; bearing habitus mainly on 1 year old shoots and subsequently on 2-3 years old branches (like 'Bartlett'); partial grafting incompatibility with quince rootstocks; medium late ripening (about 15 days after 'Bartlett'); medium productivity; big size of the fruit (about 300 g) with pyriform-elongated shape (like 'Abbé Fétel'); yellow-green skin with a nice red over-color on 70-80% of surface; tender and juicy white flesh, at full ripening stage and with a very good flavor and sweet taste; long storage capacity in cold room up to 6 months.

5 Drawing Sheets

Latin name of the genus and species of the plant claimed: *Pyrus communis* L.

Variety denomination: 'PE4UNIBO'.

CROSS-REFERENCE TO RELATED APPLICATIONS

This application claims priority to European Community Plant Variety Office Plant Breeders' Rights Application No. 2014/0972 filed May 9, 2014.

BACKGROUND OF THE INVENTION

The present invention relates to a new and distinct variety of pear tree, botanically known as *Pyrus communis* L. of the Rosaceae family, and hereinafter referred to by the variety denomination 'PE4UNIBO'.

The new *Pyrus* variety is a product of a controlled breeding program conducted by the inventors, Stefano Musacchi, Silviero Sansavini and Vincenzo Ancarani, in Cadriano (Bologna), Italy. The variety is fully owned by Alma Mater Studiorum—Università di Bologna. The objective of the breeding program was to develop a new *Pyrus* variety with high fruit quality, attractive fruit with red over-color and long storability in cold room.

The new *Pyrus* variety originated from a cross made by the inventors in 1992 in Cadriano (Bologna), Italy. The female or seed parent is the *Pyrus communis* L. variety designated 'Abbé Fétel' (unpatented). The male or pollen parent is the *Pyrus communis* L. variety designated 'Cascade' (unpatented). The new *Pyrus* variety was discovered and selected by the inventors within the progeny of the stated cross in a controlled environment in 2003 in Cadriano (Bologna), Italy.

Asexual reproduction of the new *Pyrus* variety by budding and grafting was first performed in August 2003 in Cadriano (Bologna), Italy, and has demonstrated that the combination of characteristics as herein disclosed for the new variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'PE4UNIBO' which in combination distinguish this pear tree as a new and distinct variety:

1. Trees with medium vigor;
2. Medium productivity;
3. High quality fruit with good flavor;
4. Large fruit size;
5. Green-yellow skin with a nice red overcolor; and
6. Long storage capacity In comparison to the parental varieties 'Abbé Fétel' and 'Cascade', the claimed variety differs primarily in the traits listed in Table 1.

TABLE 1

| Trait | New Variety 'PE4UNIBO' | Female Parent 'Abbé Fétel' (unpatented) | Male Parent 'Cascade' (unpatented) |
|---|---|---|---|
| Compatibility with quince rootstock | Partially | Partially | Partially |
| Fruit Shape | Pyriform elongated | Pyriform elongated | Turbinate |
| Fruit Size | Large | Large | Large |
| Skin color | Green-yellow with red overcolor on 90% of skin | Yellow | Yellow with red overcolor |
| Taste | Sweet | Sweet | Sweet |
| Harvest time | Medium late (15 days after 'Bartlett' pear) | Late (30 days after 'Bartlett' pear) | Late (20 days after 'Bartlett' pear) |

Of the many commercial varieties known to the present inventor(s), the most similar in comparison to the new *Pyrus* variety 'PE4UNIBO' is the *Pyrus* variety 'Bartlett' (unpatented), in the following characteristics described in Table 2:

TABLE 2

| Characteristic | New Variety 'PE4UNIBO' | Comparison Variety 'BARTLETT' |
|---|---|---|
| Growth habit | Semi-upright | Upright |
| Compatibility with quince rootstock | Partially | Partially |
| Skin color | Green-yellow with red overcolor on 90% of skin | Yellow |
| Fruit Shape | Pyriform elongated | Pyriform elongated |
| Size | Large | Large |
| Harvest time | Medium late (15 days after 'Bartlett' pear) | Late (30 days after 'Bartlett' pear) |

BRIEF DESCRIPTION OF THE DRAWINGS

The accompanying photographs illustrate the overall appearance of the new *Pyrus* variety 'PE4UNIBO' showing the colors as true as is reasonably possible with colored reproductions of this type. Colors in the photographs may differ slightly from the color values cited in the detailed botanical description, which accurately describe the color of 'PE4UNIBO'.

DETAILED BOTANICAL DESCRIPTION

Figure 1:
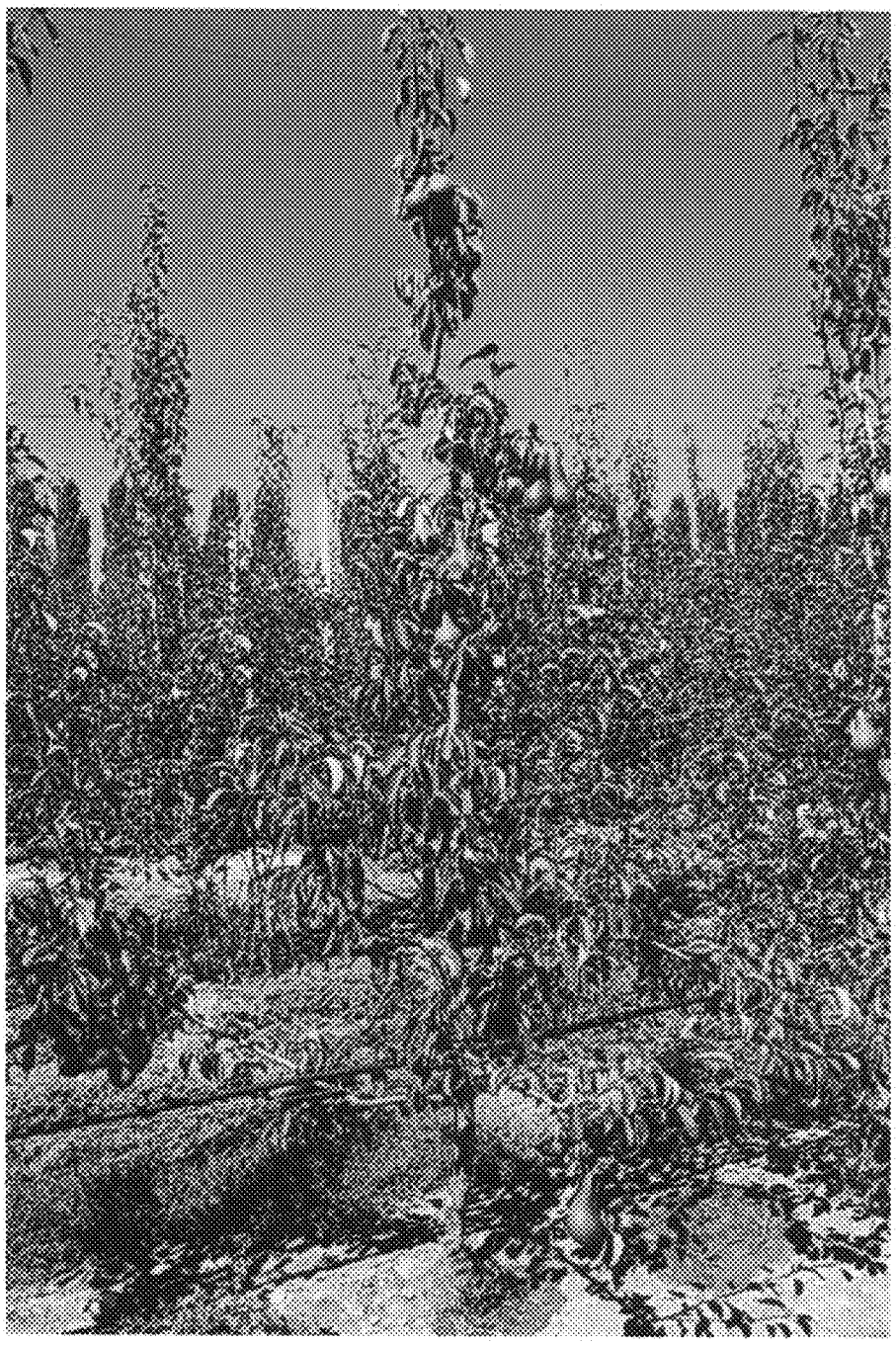
FIG. 1—shows a tree of 'PE4UNIBO', at six years old.
Figure 2:
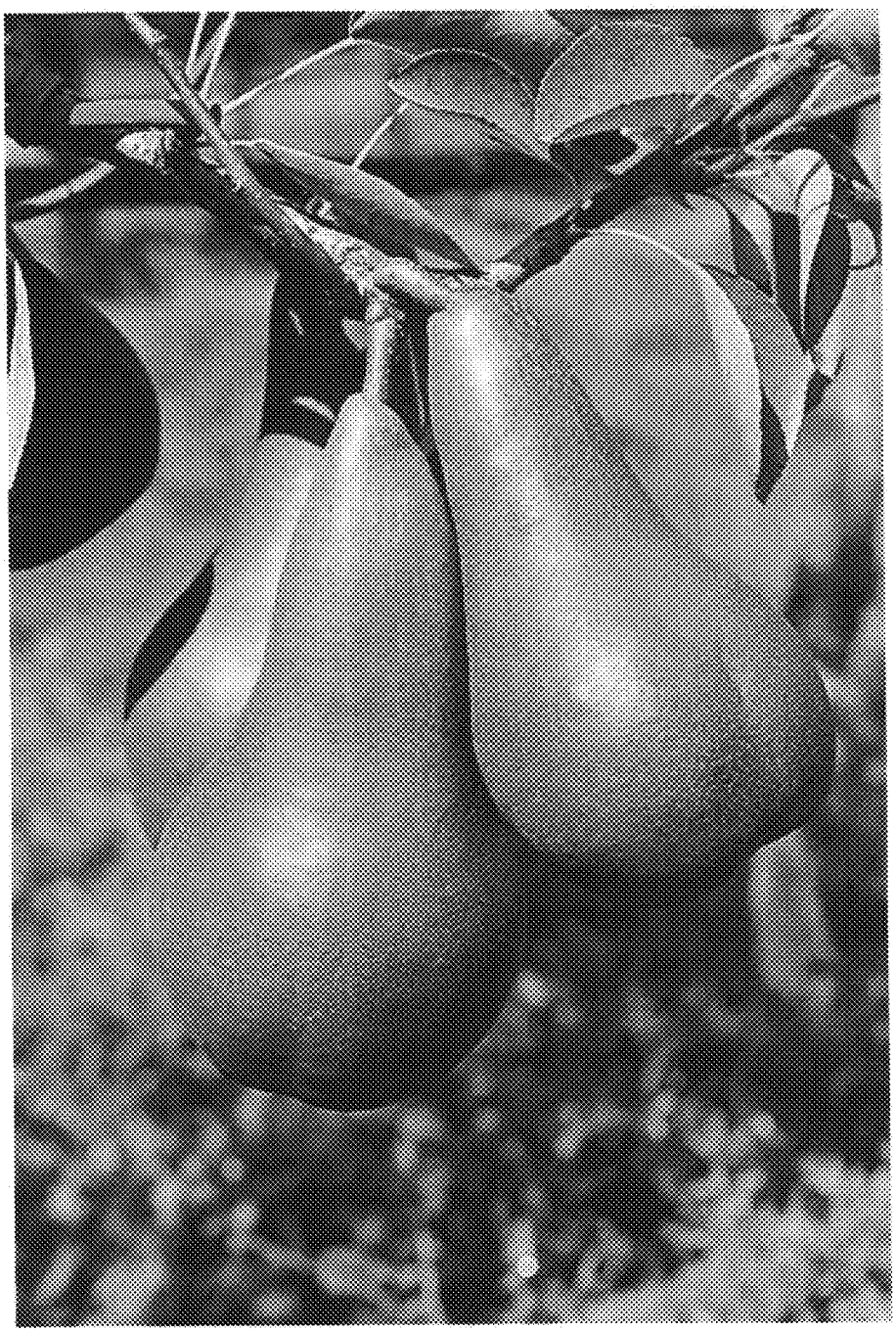
FIG. 2—shows typical fruits of 'PE4UNIBO'.
Figure 3:
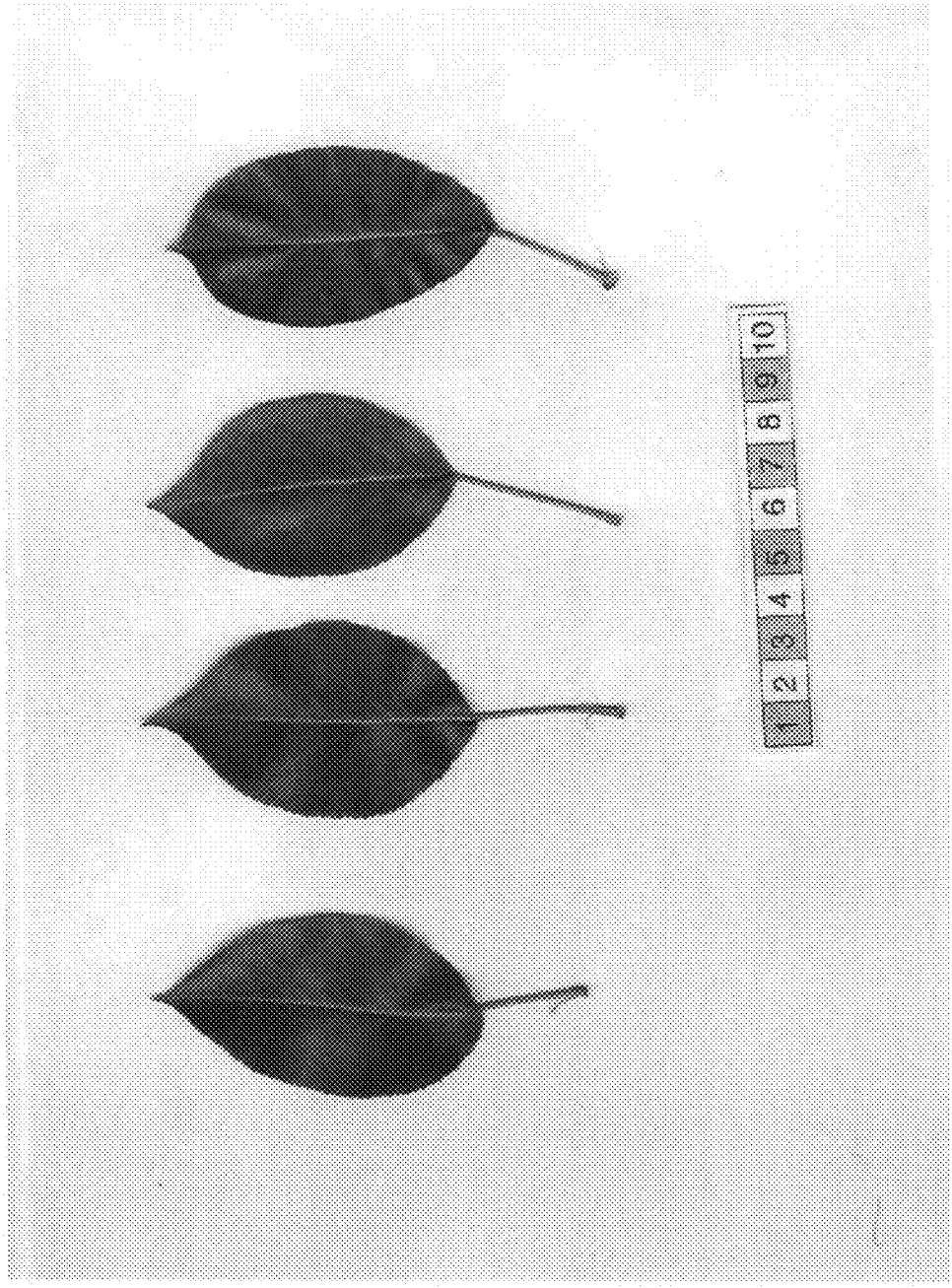
FIG. 3—shows the leaves of 'PE4UNIBO'.
Figure 4:
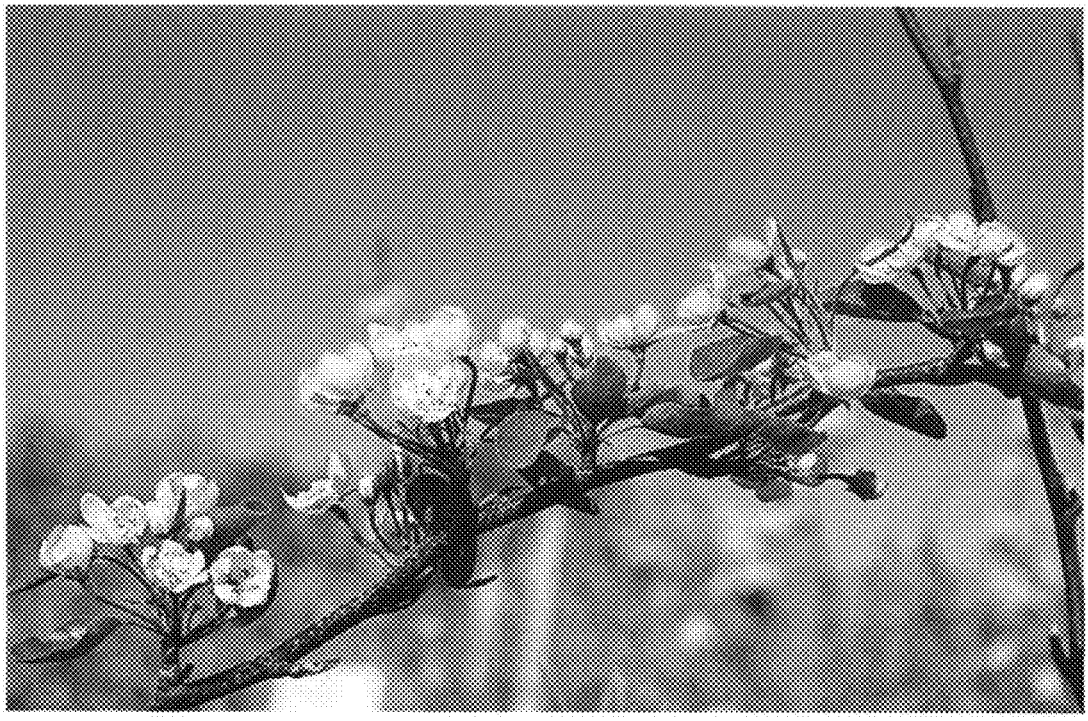
FIGS. 4 and 5—show different images of the flowers of 'PE4UNIBO', at full bloom.
Figure 5:
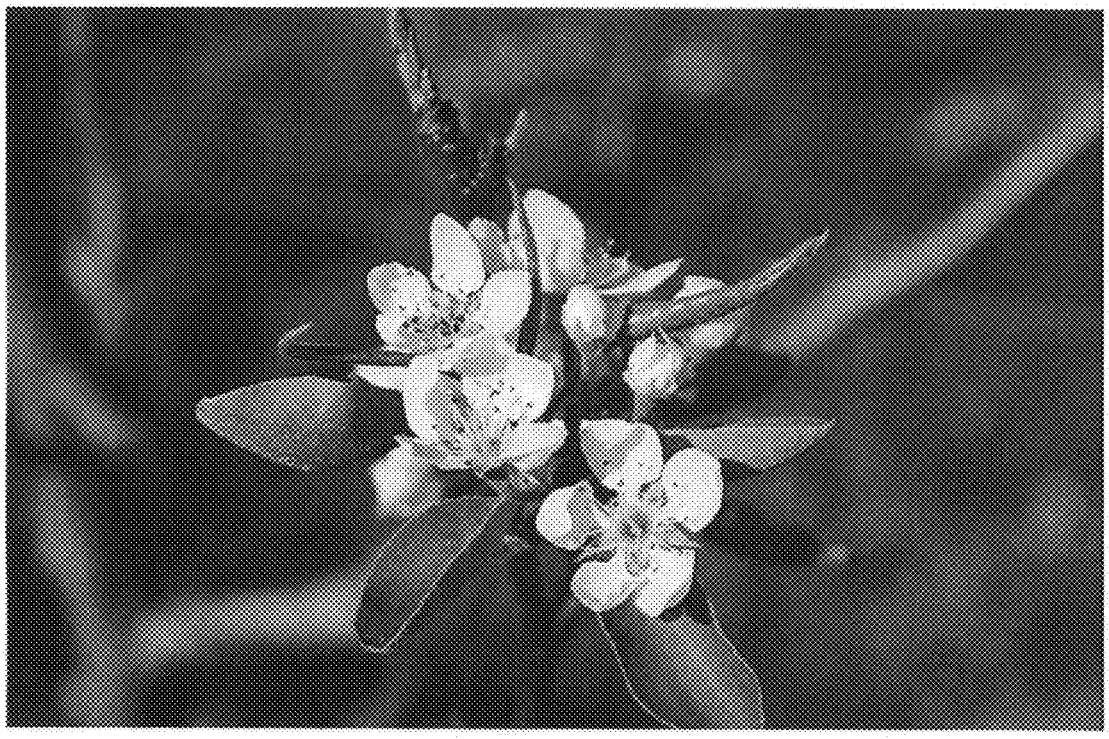

The new *Pyrus* variety 'PE4UNIBO' has not been observed under all possible environmental conditions. The phenotype of the new variety may vary with variations in environment such as temperature, light intensity, and day length without any change in the genotype of the pear tree.

The aforementioned photographs, together with the following observations, measurements and values describe trees of 'PE4UNIBO' as grown in the pear farm in Cadriano (Bologna), Italy, under conditions which closely approximate those generally used in commercial practice. The pear farm in which PE4UNIBO is growing has a clay soil; the climate is temperate continental with high summer temperatures and low winter temperatures; the orchard has a drip irrigation system used for fertigation.

Unless otherwise stated, the detailed botanical description includes observations, measurements and values based on six years old 'PE4UNIBO' trees grown in the pear farm in Cadriano (Bologna), Italy from 2009 to 2014. Quantified measurements are expressed as an average of measurements taken from a number of trees of 'PE4UNIBO'. The measurements of any individual tree, or any group of trees, of the new variety may vary from the stated average.

Color references are made to The Royal Horticultural Society Colour Chart (R.H.S.), except where general colors of ordinary significance are used. Color values were taken under daylight conditions at approximately 10:00 am in Cadriano (Bologna), Italy.

All of the trees of 'PE4UNIBO', insofar as they have been observed, have been identical in all the characteristics described below.

Classification:

*Botanical.*—*Pyrus communis* L.

*Commercial.*—*Pyrus* cv. PE4UNIBO.

Parentage:

*Female or seed parent.*—*Pyrus* variety designated 'Abbé Fétel' (unpatented).

*Male or pollen parent.*—*Pyrus* variety designated 'Cascade' (unpatented).

Propagation: Budding and grafting.

Growing conditions:

*Light intensities.*—Full sunlight.

*Temperature* (*in the vegetative season, from March to September, year* 2013).—Minimum: 0.1° C. in March. Maximum: 38.9° C. in August. Medium: 8° C. (March) to 26.3° C. (July).

*Fertilization.*—A balanced fertilizer with level of N 80 kg/ha; $P_2O_5$ 50 kg/ha; $K_2O$ 120 kg/ha.

*Growth regulators.*—Not used.

*Pruning or trimming requirements.*—Winter pruning.

Tree:

*Age.*—Observed trees were six years old and grafted on quince Rootstock BA29 with interstem of Burré Hardy pear.

*Vigor.*—Medium vigor; early bearing; late and medium flowering; medium productivity; no biennial bearing. Partially compatible with quince when grafted on it.

*Type of bearing.*—In the early years bears fruit mainly on one year old shoots then on 2-3 years branches (like 'Bartlett').

*Form.*—Semi-Upright habitus and conical branches inserted with a narrow crotch angle. Form depends on the training system used.

*Habit.*—Semi-upright habitus. Medium-high sized tree with one trunk and one leader; main branches spreading laterally semi-upward but the new growth is upright; symmetrical crown and rounded shape. The one year old shoots have a "zig-zag" growth pattern.

*Branching habit.*—Main branches angle is 35° to 75° with respect to trunk if allowed to grow naturally. The crotch angle changes along the trunk: the basal branches have a more right crotch angle whereas the upper and apical branches have a more narrow crotch angle.

*Density.*—Medium-low density.

*Size at maturity.*—Height: About 3 m. Spread: About 1.55 m.

*Trunk.*—Height (up to leaders): About 2.7 m. Diameter: About 51.3 mm (measured 20 cm above the grafter point). Texture: At first, it is smooth with numerous lenticels, then it shows numerous rough lenticels and with cracking and scaly appearance. Bark color: Primarily RHS 197C with RHS 187A under bark. Trunk Lenticels (irregular from rounded to elongated): Length: About 3.3 mm (from 0.85 to 6.02 mm). Width: About 1.1 mm (from 0.34 to 1.63 mm). Color: RHS 197A. Density: 2.01 n°/cm$^2$.

*Branches,*—Number per tree: About 14 (from 10 to 17). Length: Varies due to pyramidal shape of tree; maximum of 70 cm to 110 cm; minimum of 15 cm to 50 cm. Diameter: About 10.3 mm to 27.6 mm. Surface texture: The 2 years old branches are smooth; thereafter the 3 years old branches show a rough surface with numerous scaly lenticels. Pubescence: Absent.

*Color.*—Mature (after about 3 years old): RHS 201B (sunny side); RHS 201A (shady side). New Growth: RHS 176A (sunny side); RHS 177B (shady side). Internode length (in the middle of branches): About 3.0 cm (About 2.5 cm to 4 cm). Internode diameter (in the middle of branches): About 4.5 mm (About 3.8 mm to 5.2 mm). Branch lenticels: rounded. Length: About 1.45 mm. Width: About 1.63 mm. Color: RHS 168C. Density: 1.95 n°/cm$^2$. One year old shoot lenticels (from elliptic to rounded): Length: About 0.87 mm to 2.57 mm. Width: About 0.8 mm to 1.17 mm. Color: RHS 168D. Density: 2.6 n°/cm$^2$.

*Spur.*—Present: Yes. Distance between each spur: On the 3 years old branches, the distance is about 25 mm to 50 mm. Diameter of each spur: About 3.92 mm. Number of fruit per spur: About 1 to 3.

*Leaves.*—Arrangement: Alternate; in the new shoot there are multiple leaves (normally 3), petiolated; arranged upwards in relation to the shoot.

*Lamina.*—Size: Length: About 60.2 mm (from 48 to 82 fully expanded leaf). Width: About 40.1 mm (from 27 to 62 fully expanded leaf). Length/width ratio: 1.5. Overall Shape: the shape of leaf blade is oval-obovate with a medium-short pointed tip; the leaf area is medium-small: 19.4 cm$^2$; the longitudinal axis is medium curved. Base shape: right-angled. Apex shape: from right-angled to obtuse. Margin: bluntly serrate with a medium depth of incisions of margin. Texture: Upper surface: glabrous. Under surface: glabrous. Pubescence: Upper surface: absent. Under surface: absent. Color (mature leaves): Upper surface: RHS 147A. Under surface: RHS 147C. Color (immature leaves): Upper surface: RHS 146A. Under surface: RHS 147C.

*Venation.*—Type: pinnate venation from central vein to the leaf edge. Color: RHS 153A.

*Petiole.*—Length: About 25.7 mm. Diameter: About 10.2 mm. Color: RHS 144C.

*Stipule.*—Arrangement: present; normally arranged at the base of the petiole. Length (distance of stipules from basal attachment of petiole): About 0 mm to 10 mm. Width: About 4 mm to 17 mm.

Inflorescence:

*Blooming time.*—Full bloom on about April 5$^{th}$ (late flowering).

*Blooming period.*—About 7 to 10 days.

*Fragrance.*—Not detected.

*Type.*—Corymb.

*Number of flowers per inflorescence.*—About 4 to 6.

*Inflorescence size.*—Diameter: About 9 cm. Depth: About 6 cm.

*Buds.*—Terminal Buds: Number per spur: About 1 to 2. Shape: large and pointed. Length: About 6.98 mm. Width: About 4.53 mm. Color: Apex, RHS 165A and base, RHS 165A. Texture: Slightly tomentose; the bud support is medium sized. Pubescence: present; RHS 167A. Lateral Buds: Number per spur: About 1. Shape: medium size and pointed; the position of vegetative bud in relation to shoot is slightly held out; the bud support has generally a medium size. Length: About 5.67 mm. Width: About 2.94 mm. Color: Apex, RHS 165A, and base, RHS 165A. Texture: slightly tomentose. Pubescence: RHS 167A. Flower Buds (on 2 years old branches): Number per spur: 1. Shape: small and pointed. Length: About 6.98 mm. Width: About 3.44 mm. Color: RHS 165A.

*Petals.*—Number per flower: Five. Overall shape: the margins of petals touch each other. Apex shape: rounded to elongated. Base shape: rounded. Texture (upper surface): smooth. Texture (lower surface): smooth. Margin: entire, slightly corrugated.

*Sepals.*—Number per flower: Five.

Fruit:

*Keeping quality.*—The fruit keeps well on the tree; The fruit can be stored in cold temperature conditions for up to 6 months without loss of firmness and juiciness. The shelf life ranges from one to two weeks without having a loss of firmness and juiciness.

*Maturity when described.*—Ripe for eating.

*Maturity period after full bloom.*—About 142 days after full bloom on August 25$^{th}$.

*Type.*—Pome.

*General shape.*—Pyriform elongated (like 'Abbé Fétel'), with the maximum diameter clearly towards calyx; the fruit profile is concave. The stem ranges from medium-large to large, sometime without the stalk cavity. The skin shows a red over-color on the 70-80% of surface and slight russeting. The lenticels are medium-small and rusty. Average weight: About 303 g.

*Fruit size.*—Average height: About 114.7 mm. Average diameter (at widest point): About 67.0 mm. Height/thickness ratio: 1.7.

*Stem.*—Length: About 25.4 mm. Diameter: About 6.4 mm. Color: RHS 199A.

*Basin.*—Depth: About 8.2 mm. Width: About 22.3 mm.

*Calyx.*—Depth: About 5.3 mm. Width: About 5.6 mm. Crowning at calyx end: weak. Calyx tube: Closed (it does not communicate with locules); at harvest, the sepals are converging or erect.

*Skin.*—Thickness: medium. Texture: smooth to slightly rough. Color: ground color: RHS 153A; over-color: RHS 178B. Lenticels: rounded and rough. Length: About 1.38 mm. Width: About 1.27 mm. Color: RHS 197A. Density: 24 n°/cm$^2$.

*Flesh.*—Firmness (at picking time): 5.5 to 6.5 kg/cm$^2$. Color: RHS 157C. Texture: fine, tender and juicy. Aroma: rather aromatic, good flavor and sweet taste. Sugar content (at picking time): 13.1 to 13.6° Brix. Acidity/Starch (at picking time) 3.75 to 3.79 g/lt malic acid. Core: Symmetry of core: slightly asymmetric. Distinctness of core lines: medium. Locules:

Number (per fruit): 5. Length: About 17.8 mm. Width: About 8.35 mm. Form: open.

Seeds:

*Number per fruit.*—About 2 to 10.

*Number per locule.*—About 2.

*Shape.*—Elliptic.

*Length.*—About 11.1 mm.

*Width.*—About 5.4 mm.

*Texture.*—Smooth.

*Color.*—RHS 165A.

Use: Fresh market.

Disease/pest resistance: Unknown; test for tolerance to Fire Blight (*Erwinia amylovora*) in progress.

Disease/pest susceptibility: None observed.

Winter hardiness: No winter cold damage to wood and buds of dormant pear trees have been observed during the years; but open flowers and young fruitlets are killed by exposure to −1.5 to −3° C., depending on the length of exposure.

Drought/heat tolerance: Tolerant to temperatures up to 38° C., growth is limited by drought periods without irrigation.

What is claimed is:

1. A new and distinct variety of *Pyrus communis* L. pear tree named 'PE4UNIBO', as illustrated and described herein.

* * * * *